United States Patent [19]
Petrillo

[11] Patent Number: 5,616,924
[45] Date of Patent: Apr. 1, 1997

[54] OPTICAL ENHANCEMENTS TO SCINTILLATING SYSTEMS USING DYNAMICALLY CONTROLLED MATERIALS

[75] Inventor: Micheal J. Petrillo, Twinsburg, Ohio

[73] Assignee: Picker International, Inc., Highland Heights, Ohio

[21] Appl. No.: 543,288

[22] Filed: Oct. 16, 1995

[51] Int. Cl.$^6$ .............................. G01T 1/164; G01T 1/20
[52] U.S. Cl. ............................................................ 250/368
[58] Field of Search .............................................. 250/368

[56] References Cited

U.S. PATENT DOCUMENTS

| | | | |
|---|---|---|---|
| 3,683,180 | 8/1972 | Martone et al. | 250/71.5 |
| 3,950,648 | 4/1976 | Martone et al. | 250/369 |
| 4,090,081 | 5/1978 | Takami et al. | 250/368 |
| 4,109,150 | 8/1978 | Martone et al. | 250/368 |
| 4,145,609 | 3/1979 | Takami et al. | 250/361 R |
| 5,091,650 | 2/1992 | Uchida et al. | 250/368 |
| 5,150,394 | 9/1992 | Karellas | 250/368 |
| 5,305,126 | 4/1994 | Kobayashi et al. | 359/52 |

OTHER PUBLICATIONS

"Performance of a Position–Sensitive Scintillation Detector", Karp, et al. Phys. Med. Biol, 1985, V. 30, N. 7, pp. 643–655.

"Polymer Dispersed Nematic Liquid Crystal For Large Area Displays and Light Valves", Drzaic, J. Appl. Phys. 60 (6) 15 Sep. 1986 pp. 2142–2148.

"Design of an Efficient Position Sensitive Gamma Ray Detector For Nuclear Medicine", Rogers, et al., Phys. Med. Biol., 1986 V. 31, N. 10, pp. 1061–1090.

"Field Controlled Light Scattering From Nematic Microdroplets: A New Display Technology", Doane, et al.

*Primary Examiner*—Carolyn E. Fields
*Attorney, Agent, or Firm*—Fay, Sharpe, Beall, Fagan, Minnich & McKee

[57] ABSTRACT

A scintillator crystal (22) for a diagnostic device (10) has a reflective surface which is dynamically adjustable. Radiation (42) from a diagnostic scan enters a detector (14a, 14b, 14c) and strikes the scintillator crystal (22). The scintillator crystal (22) converts the radiation into a plurality of scintillations or light photons (26) which travel in all directions. A plurality of photomultiplier tubes (30) are optically coupled to an optically transmissive plate (28) which is optically coupled to an exit surface of the scintillator crystal. The entrance surface of the scintillator crystal is polished and laminated with a liquid crystal layer (54). The liquid crystal layer has light dispersion and reflectivity properties which are dynamically adjustable in response to electrical (62) or chemical stimuli. The liquid crystal layer is adjustably electrically biased to adjust a solid angle with which optical photons are reflected back towards the photomultiplier tubes to optimize a light spread function or solid angle of reflection.

22 Claims, 3 Drawing Sheets

OPTICAL ENHANCEMENTS TO SCINTILLATING SYSTEMS USING DYNAMICALLY CONTROLLED MATERIALS

BACKGROUND OF THE INVENTION

The present invention relates to the radiography art. It finds particular application in conjunction with diagnostic imaging devices such as computerized tomographic (CT) scanners, single photon emission computed tomography (SPECT), and positron emission tomographic (PET) scanners. However, it is to be appreciated that the present invention may also find application in conjunction with other radiation treatment apparatus and imaging apparatus.

Nuclear cameras generally include radiation detectors which collect radiation transmitted through or emitted from a subject. The detector typically has a scintillation crystal constructed of a large doped sodium iodide crystal. The scintillation crystal is hermetically sealed between a glass plate and an aluminum case. The surface of the scintillation crystal toward the glass plate is polished and optically coupled to the glass plate. The glass plate is in turn, optically coupled with an array of photomultiplier tubes. The opposite surface of the scintillation crystal is treated such that it internally reflects light with a preselected solid angle. The reflective surface is sanded with a preselected sanding pattern and coated with a reflective or semi-reflective material, e.g. Teflon. In this manner, the scintillation crystal is manufactured with a fixed solid angle of reflection.

During a scan, gamma rays enter the detector through a collimator mounted on the face of the detector. The gamma rays strike the scintillation crystal causing the scintillation crystal to scintillate, i.e., emit light photons in response to the gamma radiation. The photons initially travel uniformly in all directions of the scintillation crystal. Some photons travel directly out of the scintillation crystal through the glass plate and into the photomultiplier tubes. Other photons travel back towards the treated reflective surface at the entrance of the scintillation crystal. The reflective surface reflects the photons back towards the photomultiplier tubes. In order to obtain a strong signal for each scintillation event, it is advantageous to have most of the photons generated processed by the photomultiplier tubes. However, it is undesirable to reflect the light back too steeply, and it is also undesirable to reflect the light too diffusely. The angle of reflection is dependant on the size and geometry of the photomultiplier tubes and the thickness of crystal/light pipe (LP).

This reflection technique has some disadvantages. Particularly, the sanding process is a difficult precision process. It is difficult to sand the crystal surface such that the entire surface of the scintillation crystal has the same index of reflectivity.

Other difficulties involve the scintillation crystals light spread function. The spatial resolution of the gamma camera is directly related to the light spread function within the scintillation crystal. The light spread function is dictated by the surface treatment of the crystal's entrance surface. The surface treatment creates a general solid angle of reflection. The reflective properties are determined according to a particular size and geometry of the photomultiplier tube array. Changing the geometry of the photomultiplier tube array or crystal/light pipe thickness requires painstaking modifications to the reflective surface to optimize the light spread function.

A uniform index of reflectivity over the entire surface is not necessarily ideal. The array of photomultiplier tubes on the opposite surface defines a mosaic of high, low, and intermediate light sensitive regions.

The present invention provides a new and improved scintillation crystal assembly and nuclear camera which overcomes the above-referenced problems and others.

SUMMARY OF THE INVENTION

In accordance with the present invention, a scintillation crystal having a dynamically adjustable reflective surface is provided.

A diagnostic imaging device includes a scintillation crystal which generates light in response to received radiation. A plurality of photomultiplier tubes are optically coupled to the scintillation crystal. A processor circuit for processes signals from the photomultiplier tubes into a diagnostic image. A liquid crystal layer is optically connected with the scintillation crystal.

In accordance with a more limited aspect of the present invention, the liquid crystal is constructed of a polymer which includes a plurality of nematic liquid crystal droplets. Each droplet has an optical axis which is selectively changeable by an electric field. Applying the electric field selectively aligns the optical axes of the droplets to adjust a selected solid angle of reflection.

In accordance with a more limited aspect of the present invention, an electrically conductive grid is connected to the liquid crystal layer. A power source is electrically connected to the electrically conductive grid. The power source generates an electric field in selected portions of the grid which affects the optical axes of the liquid crystal droplets near the selected portions of the grid.

In accordance with a yet more limited aspect of the present invention, the scintillation crystal has two polished surfaces. The liquid crystal layer is optically coupled to one of the polished surfaces.

In accordance with another aspect of the present invention, a method of diagnostic imaging, with a diagnostic imaging device including a scintillation crystal is provided. At least one of transmission and emission radiation is received. The received radiation is converted into light photons. A portion of the light photons are selectively reflected with at least one angle of reflection. The light photons are detected and signals indicative of the light photons are generated. A volumetric image is then generated from the signals.

One advantage of the present invention is that it provides for a dynamically adjustable reflective surface for a scintillation crystal.

Another advantage of the present invention is that the light spread function of the scintillation crystal is readily optimized.

Another advantage of the present invention is that it eliminates the reflectivity adjusting treatment of the surface of the crystal.

Another advantage of the present invention resides in a freedom to adjust the light spread function of the surface by electrical and chemical stimuli.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
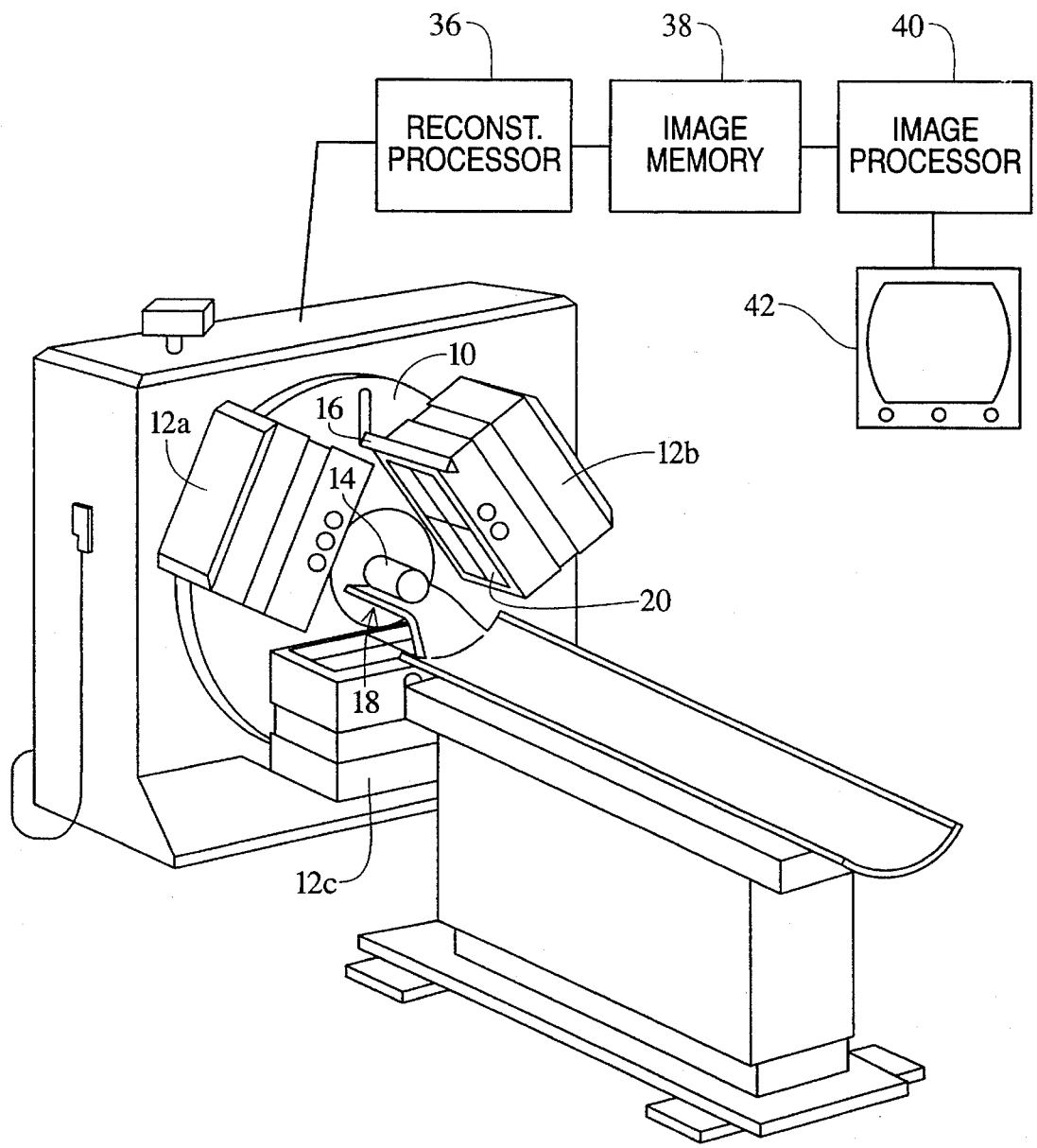
FIG. 1 is a diagrammatic illustration of a nuclear imaging system according to the present invention.

With reference to FIG. 1, a diagnostic imaging system includes a gantry 10 which supports one or more radiation detectors 12a, 12b, 12c. The radiation detectors collect radiation which is emitted from a subject 14 or transmitted from a transmission radiation source 16 across a subject receiving region 18 through the subject 14, or both. Each detector typically includes a collimator 20 mounted on a radiation receiving face of the detector. The collimator limits the radiation received by the detector to only radiation travelling along a selected path such as parallel rays.

Figure 2:
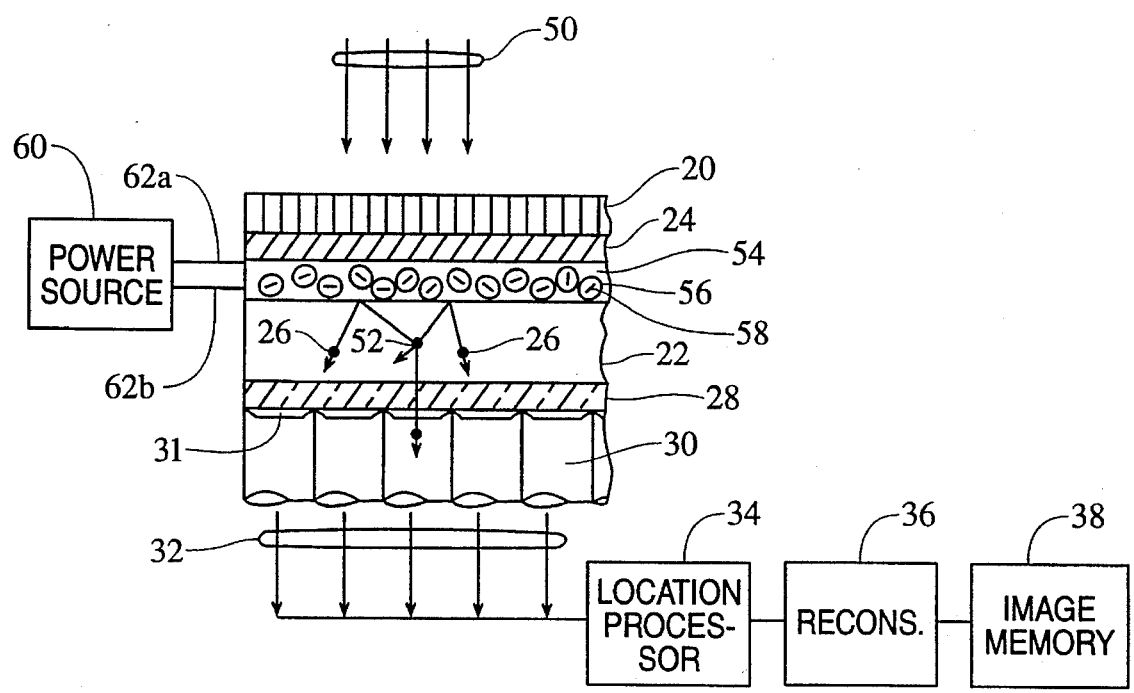
FIG. 2 illustrates construction of the detector heads of FIG. 1.

With reference to FIG. 2, each detector includes a scintillation crystal 22 which is mounted behind the collimator 20 and enclosed by a metallic case 24, such as an aluminum case. The scintillation crystal 22 converts the radiation received by the detector into light photons 26. In the preferred embodiment, the scintillation crystal 22 is a thallium doped sodium iodide (NaI) crystal. An optically transmissive plate 28, such as glass, optically couples an array of photodetectors such as photomultiplier tubes 30 to the scintillation crystal. The plate 28 may be further optically coupled to the photomultiplier tubes 30 such as by a light pipe 31 which adjusts an amount of photons entering the tubes 30. The photomultiplier tubes 30 receive the photons generated by the scintillation events and generate corresponding electrical signals 32. A location processor 34 collects the signals 32 and determines a spatial location, typically an x,y-coordinate, of each scintillation event as well as its energy, typically as a z-coordinate. A reconstruction processor 36 processes detector head position information and x,y-coordinate information into three-dimensional volume images, two-dimensional slice images, and projection images, as is known in the art. The processed electronic images are accumulated and stored in an image memory 38. A video or image processor 40 converts the electronic image representations into appropriate form for display on a human-readable display 42.

During a scan, radiation, such as γ radiation photons 50, entering the scintillation crystal is converted into light photons or scintillations at various points and at various depths within the scintillation crystal 22. At a particular scintillation point 52, the generated light photons 26 travel uniformly in all directions. Because the generated light photons travel in all directions, many photons travel in directions away from the photomultiplier tubes 30. To reduce the number of lost light photons, the receiving surface of the scintillation crystal 22 is polished and a liquid crystal layer 54 is laminated to it.

The liquid crystal 54 is preferably a polymer dispersed liquid crystal material (PDLC). Nematic droplets 56 are distributed and suspended in a polymer matrix throughout the liquid crystal material 54. Each droplet has an optical axis represented by a line 58 whose directional alignment determines light scattering properties of the liquid crystal 54.

In one embodiment, an energy source 60 selectively applies a voltage through leads 62a and 62b across the liquid crystal 54 creating a uniform electric field. The electric field manipulates the optical axes 58 of the liquid crystal droplets 56 into a selected alignment. By changing the alignment of the liquid crystal droplets 56, the liquid crystal layer 54 reflects light at a greater or lesser solid angle of reflection. In this manner, light photons generated within the scintillation crystal 22 which travel away from the photomultiplier tubes 30 are reflected by the liquid crystal layer 54 back towards the photomultiplier tubes 30 with an electronically adjustable solid angle.

Figures 3A, 3B:
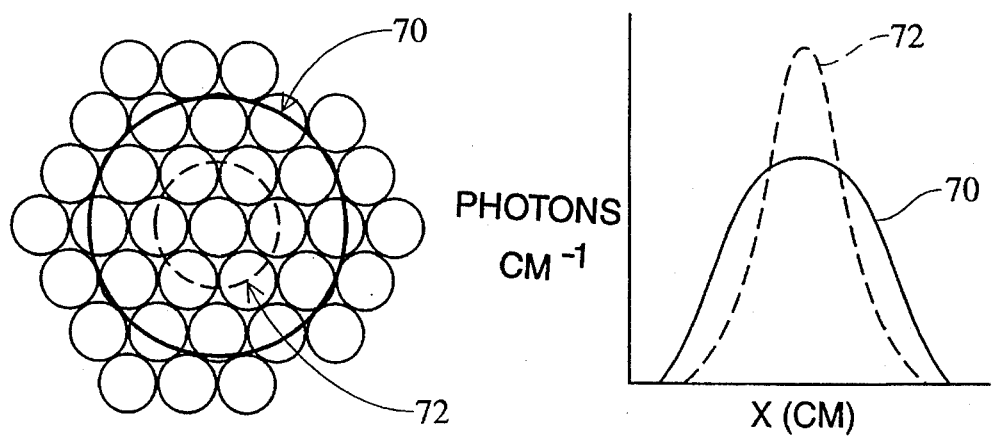
FIGS. 3A and 3B are an illustration of a variable light spread function of the scintillator shown in FIG. 2 for a geometry of photomultiplier tubes.

With reference to FIGS. 3A and 3B, the scintillation crystal 22 has a light spread function (LSF) which is characterized by the light scattering properties caused by the angle at which light is reflected off the liquid crystal layer 54 and onto the photomultiplier tubes 30. For a particular geometry of photomultiplier tubes 30, the spatial resolution of the detector is closely tied to the light spread function. By applying an electric field of a first voltage level to the liquid crystal, the liquid crystal diffusely reflects light resulting in a wide light spread function shown by a wide cone base or circle 70 relative to the photomultiplier tubes 30. Changing the electric field to a second voltage level causes the liquid crystal 22 to become specular, resulting in a narrow light spread function shown by dotted cone base or circle 72. For the geometry of photomultiplier tubes 30 shown in FIG. 3, the optimal light spread function is between circle 70 and circle 72. The light spread function is adjusted by changing the electric field to the liquid crystal, thus changing the solid angle of reflection. In this fashion, the light spread function of the scintillation crystal 22 and the spatial resolution of the detector is easily fine tuned. Should the geometry of the photomultiplier tubes 30 or crystal/light pipe thickness be changed, the light spread function of the scintillation crystal is dynamically adjusted by changing the electric field to the liquid crystal, thus optimizing the light spread function for the particular geometry.

Figure 4:
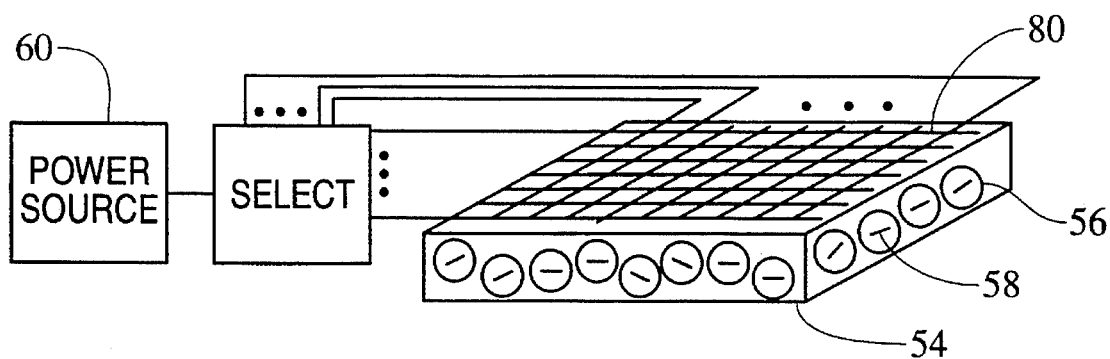
FIG. 4 is an illustration of a liquid crystal layer with an electrically conductive grid connected thereto in accordance with the present invention.

In an alternative embodiment, with reference to FIG. 4, an electrically conductive grid 80 is connected to either side of the liquid crystal layer 54. The grid defines x,y-coordinates which are selectively activated by the power source 60 to produce an electric field at selected regions of the liquid crystal layer 54. The electric field affects the optical axes 58 of the liquid crystal droplets 56 which are positioned near the electric field. Applying various electric fields to selected regions of the liquid crystal layer, the dispersion properties, which include an angle of reflection, of the selected regions are dynamically adjustable. In this manner, deficiencies caused by variations in doping concentrations in the scintillation crystal or the like, and by variations in the photomultiplier tubes are readily adjustable.

In an alternative embodiment, the dispersion properties of the liquid crystal layer are modified chemically. The liquid crystal layer is treated with a dye to adjust the light spread function and reflectivity.

In another embodiment of the present invention, the liquid crystal layer 54 is laminated to the exit surface of the scintillation crystal 22 between the scintillation crystal 22 and the glass plate 28. Dynamically adjusting the dispersion properties of the liquid crystal controls the photon output of the scintillation crystal. The outputted photons received by the photomultiplier tubes 30 are selectively adjustable.

Figure 5:
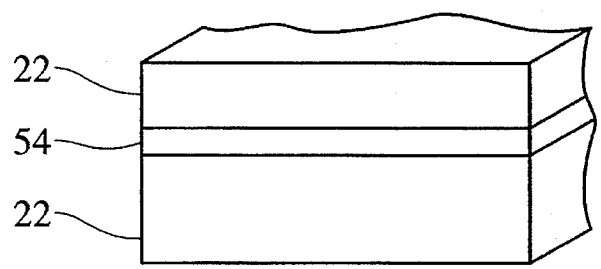
FIG. 5 is an illustration of the liquid crystal layer disposed within a scintillator crystal in accordance with the present invention; and, FIG. 6 is an illustration of a liquid crystal layer coupled to a plurality of edges of the scintillation crystal in accordance with the present invention.

With reference to FIG. 5, in yet another embodiment, the liquid crystal layer 54 is associated with the scintillation crystal 22 at a selected plane between scintillation crystal layers. The scintillation crystal layers may be used to differentiate radiation energy, may have different characteristics, or the like. Adjusting the bias on the liquid crystal layer adjust the dispersion and light transmission properties of the scintillation events.

Figure 6:
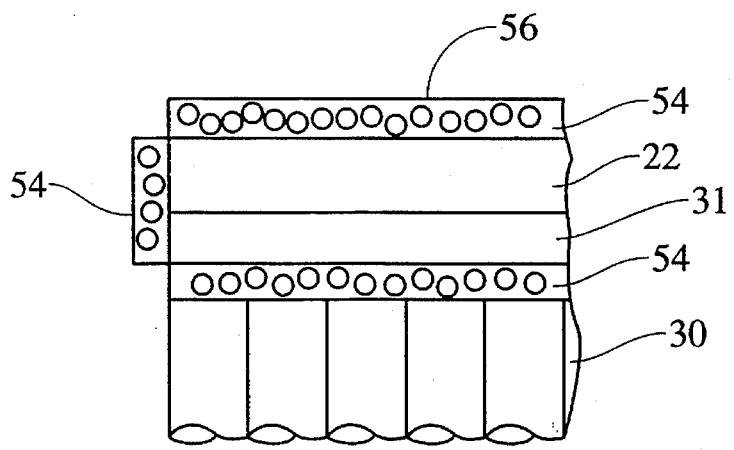

With reference to FIG. 6, in yet another embodiment, a liquid crystal layer 54 is associated with the scintillation crystal 22 at the top, the bottom, and the side edges of the scintillation crystal. Optically coupling a liquid crystal layer 54 to a plurality of edges of the scintillation crystal 22 provides for XTAL boundary control.

The invention can further be applied to any scintillating material which produces photons which are detected by photomultiplier tubes, charge-couple devices, or avalance photodiodes.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. In a nuclear camera system including radiation detectors facing an examination region which houses a support for a subject injected with a radiation emitting radiopharmaceutical, each radiation detector including a scintillation crystal which generates light in response to received radiation and having a plurality of faces, a first face of the scintillation crystal being optically coupled to at least one optical sensor and all other faces of the scintillation crystal being encased in a housing material which blocks ambient light from entering the scintillation crystal, and a reconstruction processor for processing signals from the optical sensors into a diagnostic image, the improvement comprising:

a liquid crystal layer disposed between the scintillation crystal and the housing material for selectively reflecting the light generated by the scintillation crystal.

2. In the nuclear camera as set forth in claim 1, the improvement further comprising:

the liquid crystal layer including a plurality of liquid crystal droplets suspended in a polymer, each of the plurality of liquid crystal droplets having an optical axis which is selectively changeable by an electric field.

3. In the nuclear camera as set forth in claim 2, the improvement further comprising:

an electrically conductive grid connected to the liquid crystal layer; and a power source electrically connected to each portion of the electrically conductive grid, the power source generating an electric field in selected portions of the electrically conductive grid which affects the optical axes of the liquid crystal droplets near the selected portions.

4. In the nuclear camera as set forth in claim 1, the improvement further comprising:

the scintillation crystal having two polished surfaces, the liquid crystal layer being optically coupled to one of the polished surfaces.

5. In the nuclear camera as set forth in claim 1, the improvement further comprising:

the liquid crystal layer being optically coupled to a radiation receiving surface of the scintillation crystal.

6. In the nuclear camera as set forth in claim 5, the improvement further comprising:

an electrically conductive grid connected to the liquid crystal layer; and a power source electrically connected to each portion of the electrically conductive grid, the power source generating an electric field in selected portions of the electrically conductive grid which affects light dispersion properties of the liquid crystal layer adjacent the selected portions.

7. In the nuclear camera as set forth in claim 1, the improvement further comprising:

a light pipe which optically connects the plurality of optical sensors and the scintillation crystal.

8. In the nuclear camera as set forth in claim 1, the improvement further comprising:

the liquid crystal layer being treated with a dye, the dye changing light dispersion properties of the liquid crystal layer.

9. A radiation detector for a diagnostic imaging device comprising:

a scintillation crystal having at least a radiation receiving surface and rear surface, the scintillation crystal generating light in response to the received radiation which generated light propogates toward at least the radiation receiving and rear surfaces;

an optically transmissive plate coupled to the rear surface of the scintillation crystal;

a liquid crystal coupled to at least one surface of the scintillation crystal other than the rear surface, the liquid crystal selectively adjusting reflectivity of light generated by the scintillation crystal; and, a plurality of photodetectors optically coupled to the optically transmissive plate.

10. The radiation detector as set forth in claim 9 wherein the scintillation crystal is a thallium doped sodium iodide crystal.

11. The radiation detector as set forth in claim 9 wherein the liquid crystal includes a polymer having a plurality of nematic liquid crystal droplets each having an optical axis which affects reflection of the light within the scintillation crystal.

12. The radiation detector as set forth in claim 11 further including:

a voltage source coupled to at least one portion of the liquid crystal, in response to a voltage from the voltage source, the optical axes of the plurality of pneumatic liquid crystal droplets near the at least one portion align in a selected direction to adjust the reflection of the light.

13. The radiation detector as set forth in claim 9 further including:

an electrical energy source connected with the liquid crystal for applying electrical energy to adjust light dispersion properties of the liquid crystal.

14. The radiation detector as set forth in claim 13 further including:

an electrically conductive matrix connected between the electrical energy source and selected regions of the liquid crystal for selectively adjusting the light dispersion properties of the regions independently.

15. The radiation detector as set forth in claim 9 wherein the liquid crystal is treated with a dye to adjust the reflection of the light.

16. In a nuclear camera including a scintillation crystal which generates light in response to received radiation, a plurality of optical sensors optically coupled to the scintillation crystal and a processor for processing signals from the optical sensors into a diagnostic image, the improvement further comprising:

a liquid crystal layer associated with the scintillation crystal, the liquid crystal layer being optically coupled to at least two light output surfaces of the scintillation crystal.

17. A method of diagnostic imaging comprising:

receiving radiation through a radiation receiving face of a scintillation crystal;

converting the radiation received to light photons with the scintillation crystal;

selectively reflecting a portion of the light photons within the scintillation crystal with a dynamically adjustable angle of reflection;

detecting the light photons with optical sensors and generating signals indicative of the detected light; and, generating an image representation from the signals generated.

18. The method of diagnostic imaging as set forth in claim 17 further including:

adjusting the angle of reflection with one of an electric signal and a chemical stimuli.

19. The method of diagnostic imaging comprising:

receiving radiation through a radiation receiving face of a scintillation crystal;

converting the radiation received to light photons with the scintillation crystal;

selectively reflecting a portion of the light photons with an adjustable angle of reflection using a liquid crystal coating on the radiation receiving face of the scintillation crystal; and detecting the light photons with optical sensors and generating signals indicative of the detected light; and, generating an image representation from the signals generated.

20. The method of diagnostic imaging as set forth in claim 19 further including:

applying an adjustable electric field to selected regions of the liquid crystal coating to adjust the angle of reflection for each region.

21. A radiation detector for a diagnostic imaging device, the detector comprising:

a light impermeable, radiation permeable case;

an optically transmissive plate sealed to the case to provide a light output window;

a photodetector array optically coupled to the optically transmissive plate;

a scintillation crystal sealed in the case for converting radiation passing through the case to light which light passes through the optically transmissive plate and is converted into electronic signals by the photodetector array, there being a spatially non-uniform response to the received radiation;

a liquid crystal disposed within the case, the liquid crystal being electrically controlled to compensate for the non-uniform response.

22. The radiation detector as set forth in claim 21 wherein the liquid crystal is mounted on interior surfaces of the case and is electronically controlled to adjust reflection of light from the case back into the scintillation crystal and through the optically transmissive plate.

\* \* \* \* \*